United States Patent [19]

Gier

[11] Patent Number: 5,709,203

[45] Date of Patent: Jan. 20, 1998

[54] SELF CONTAINED, CRYOGENIC MIXED GAS SINGLE PHASE STORAGE AND DELIVERY SYSTEM AND METHOD FOR BODY COOLING, GAS CONDITIONING AND UTILIZATION

[75] Inventor: Harold L. Gier, Boulder, Colo.

[73] Assignee: Aerospace Design and Development, Inc., Boulder, Colo.

[21] Appl. No.: 755,249

[22] Filed: Nov. 22, 1996

Related U.S. Application Data

[63] Continuation of Ser. No. 328,743, Oct. 24, 1994, abandoned, and a continuation-in-part of Ser. No. 480,555, Jun. 7, 1995, abandoned, which is a continuation of Ser. No. 879,581, May 7, 1992, abandoned, said Ser. No. 328,743, is a continuation-in-part of Ser. No. 879,581, abandoned.

[51] Int. Cl.$^6$ .............. A62B 7/06; A62B 17/00; A61M 15/00; F17C 7/02
[52] U.S. Cl. .............. 128/201.21; 128/201.29; 128/202.19; 128/202.11; 128/204.15; 128/204.17; 2/2.14; 2/2.15; 62/50.1
[58] Field of Search .............. 128/202.11, 204.15, 128/201.21, 201.29, 202.19, 204.17; 62/50.1, 289, 50.2; 2/2.14, 2.15, 81, DIG. 3

[56] References Cited

U.S. PATENT DOCUMENTS

| | | |
|---|---|---|
| 1,448,590 | 3/1923 | Gensecke . |
| 1,459,158 | 6/1923 | Lisse . |
| 2,460,269 | 2/1949 | Appeldoorn . |
| 3,062,017 | 11/1962 | Balcar et al. . |
| 3,064,448 | 11/1962 | Whittington . |
| 3,079,765 | 3/1963 | Le Vantine . |
| 3,085,405 | 4/1963 | Frantti . |
| 3,161,192 | 12/1964 | McCormack . |
| 3,211,216 | 10/1965 | Coleman, Jr. et al. . |
| 3,227,208 | 1/1966 | Potter, Jr. et al. . |
| 3,248,897 | 5/1966 | Stark . |
| 3,279,201 | 10/1966 | Wortz et al. . |
| 3,289,748 | 12/1966 | Jennings . |
| 3,318,307 | 5/1967 | Nicastro . |
| 3,411,156 | 11/1968 | Feher . |
| 3,430,688 | 3/1969 | Crocker . |
| 3,463,150 | 8/1969 | Penfold ................ 128/202.11 |
| 3,487,765 | 1/1970 | Lang . |
| 3,526,223 | 9/1970 | Curtis ................ 128/202.11 |
| 3,570,481 | 3/1971 | Woodberry, Jr. . |
| 3,572,048 | 3/1971 | Murphy . |
| 3,635,216 | 1/1972 | Curtis ................ 128/202.11 |
| 3,699,775 | 10/1972 | Cowans . |
| 3,736,764 | 6/1973 | Chambers et al. . |
| 3,738,367 | 6/1973 | Hardy . |
| 3,743,012 | 7/1973 | Laxo . |
| 3,744,555 | 7/1973 | Fletcher et al. . |
| 3,827,246 | 8/1974 | Moen et al. ................ 62/50 |
| 3,869,871 | 3/1975 | Rybalko et al. . |
| 4,024,730 | 5/1977 | Bell et al. . |
| 4,095,593 | 6/1978 | Webbon et al. . |
| 4,172,454 | 10/1979 | Warncke et al. . |
| 4,181,126 | 1/1980 | Hendry . |

(List continued on next page.)

OTHER PUBLICATIONS

Tzimoulis, Paul J.; "I dived on liquid air"; pp. 22–29; Skin Diver, Jun. 1967.

Primary Examiner—Kimberly L. Asher
Attorney, Agent, or Firm—Harold A. Burdick

[57] ABSTRACT

A system and method for body cooling is disclosed for use with a cryogenic mixed gas storage and delivery apparatus, the storage apparatus including a compact and lightweight dewar for containing cryogenic temperature mixed gas at supercritical pressure. The system includes a garment having a fluid circulation network thereat and a plurality of heat exchangers receiving cold mixed gas expelled from the dewar for heat exchange to cool fluid in the fluid circulation network. Different ones of the heat exchangers also provide for heat input to the dewar to maintain gas therein in a single phase and provide continued expulsion energy and for warming of the gas for end use. No electrical input for fluid circulation is required.

17 Claims, 10 Drawing Sheets

U.S. PATENT DOCUMENTS

| | | |
|---|---|---|
| 4,459,822 | 7/1984 | Pasternack . |
| 4,807,447 | 2/1989 | Macdonald et al. . |
| 4,998,415 | 3/1991 | Larsen . |
| 5,062,424 | 11/1991 | Hooker . |
| 5,092,129 | 3/1992 | Bayes et al. . |
| 5,115,859 | 5/1992 | Roebelen, Jr. et al. . |
| 5,201,365 | 4/1993 | Siegel . |
| 5,214,926 | 6/1993 | Mandin et al. . |

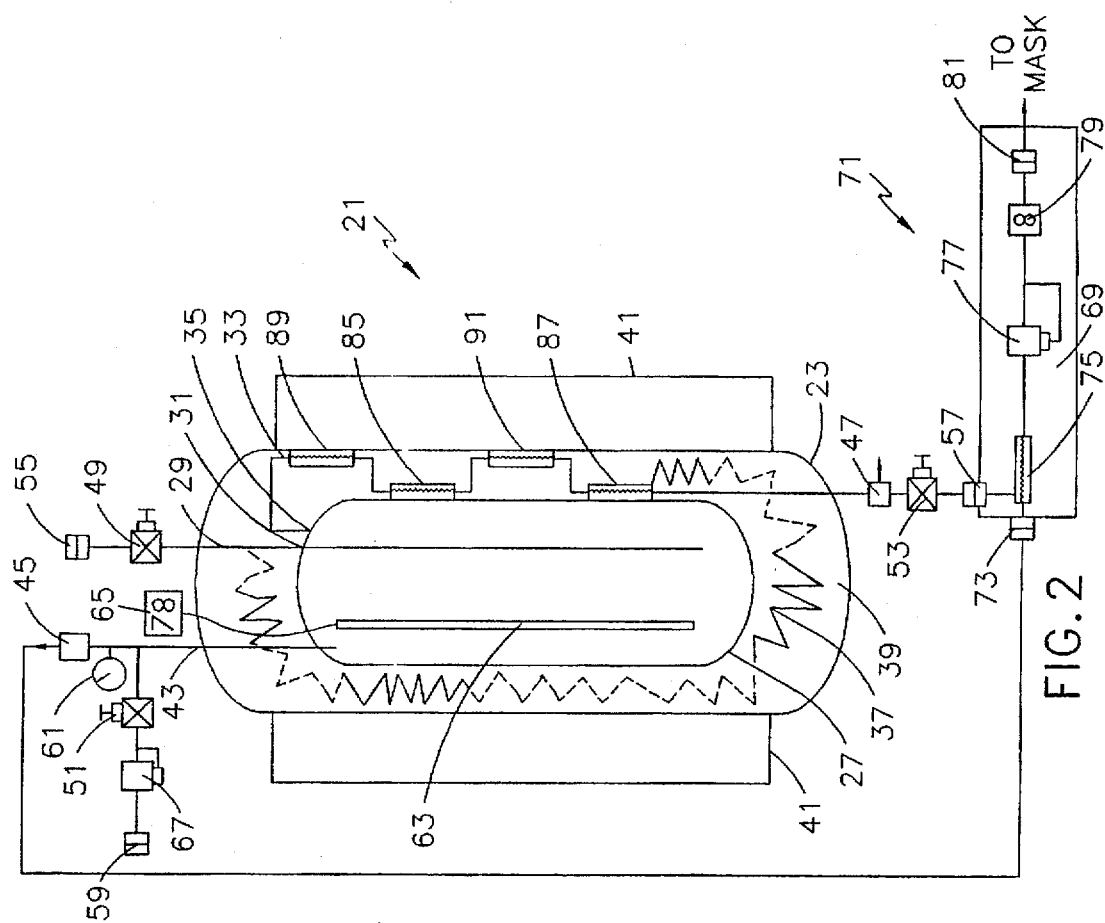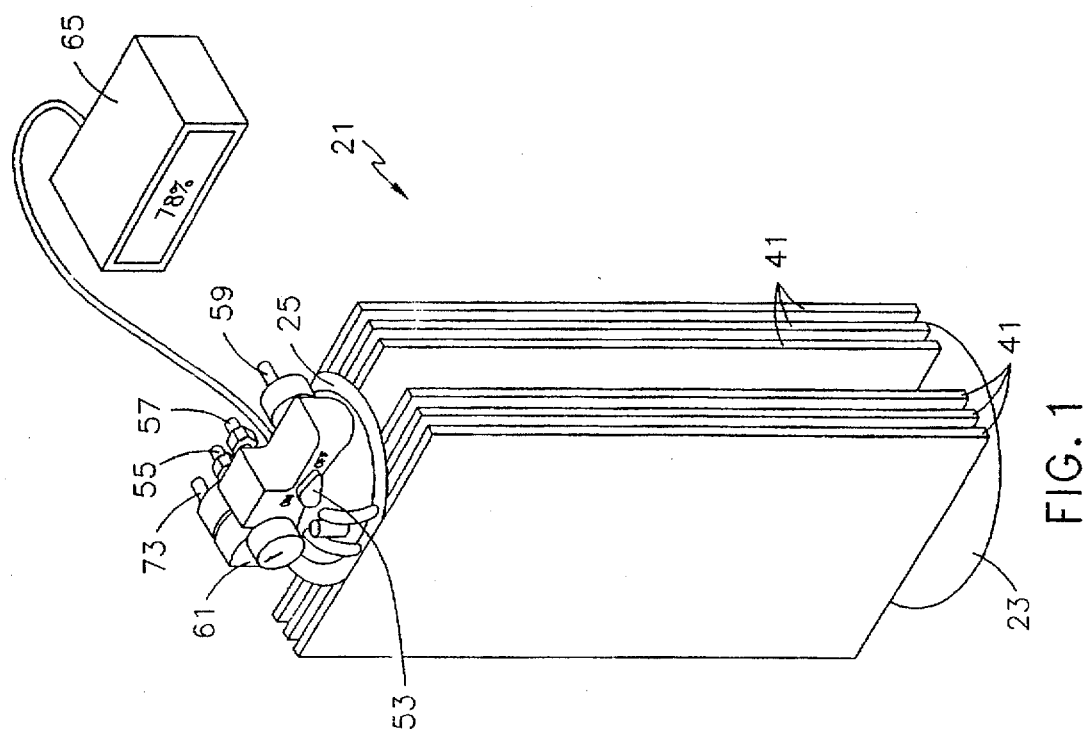

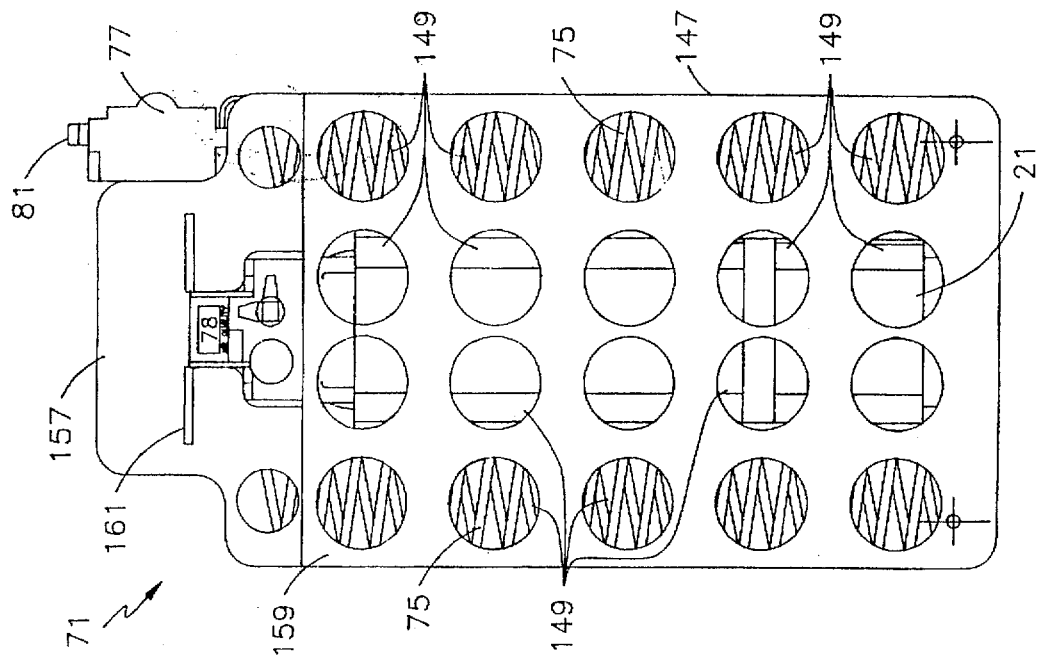

SELF CONTAINED, CRYOGENIC MIXED GAS SINGLE PHASE STORAGE AND DELIVERY SYSTEM AND METHOD FOR BODY COOLING, GAS CONDITIONING AND UTILIZATION

RELATED APPLICATION

This Application is a continuation of U.S. patent application Ser. No. 08/328,743, filed Oct. 24, 1994, now abandoned, and is a continuation-in-part of U.S. patent application Ser. No. 08/480,555 filed Jun. 7, 1995 now abandoned, which is a con of U.S. patent application Ser. No. 07/879,581 filed May 7, 1992, now abandoned, and entitled "Loading, Storage and Delivery Apparatus And Method For Fluid At Cryogenic Temperature" by Harold L. Gier and Richard L. Jetley. Said 08/328,743, Oct. 24, 1994, now abandoned, was a CIP of 07/879,581, May 7, 1992, now abandoned.

GOVERNMENT SUPPORT

This invention was made with Government support under contracts awarded by the National Aeronautics and Space Administration and the U.S. Air Force. The Government has certain rights in the invention.

FIELD OF THE INVENTION

This invention relates to body cooling and fluid storage and delivery apparatus and methods, and, more particularly, relates to integrated systems for body cooling and delivery and conditioning of mixed gas initially contained at cryogenic temperature.

BACKGROUND OF THE INVENTION

High pressure, ambient temperature gas storage and delivery devices have been heretofore suggested for providing attitude independent supply of mixed gasses such as breathable air to a user thereof. Such devices, while in use, have limited gas delivery time, are bulky, and must be operated at extremely high pressures.

Liquid air storage and delivery devices have also been suggested (see U.S. Pat. Nos. 1,448,590, 3,318,307, 3,570,481, 3,572,048, 4,181,126, 3,699,775, 1,459,158, and 3,227,208), but suffer from limited standby time due to oxygen enrichment inherent in such storage, some being unduly complex in an effort to confront this problem, are not attitude independent, and are often quite heavy.

Dispensers for cryogenic temperature elemental and compound gasses (below −175° F.) such as oxygen held for use at supercritical pressure (above 730 psia) have been heretofore suggested (see U.S. Pat. Nos. 3,062,017 and 3,827,246). In such dispensers a heat transfer mechanism (i.e., an electrical heating element or a heat exchanger) is utilized to pressurize the storage vessel having liquid oxygen loaded therein at atmospheric pressure (thus making the dispenser less than desirable as an air supply, where oxygen enrichment could occur while liquid air is in standby storage) for expelling the oxygen.

Pressure sensing is thereafter used to sense the heat transfer needs in the vessel to maintain pressure therein above critical pressure by activating the heating element periodically. Heat exchange is accomplished utilizing at least in part active means separate from the dewar thus encumbering these heretofore known dispensers with complex sensing and activating mechanisms to assure proper heat input. Improvement in such dispensers could thus still be utilized.

Liquid cooling garments for body cooling using liquid circulating through a network incorporated in the garment have also been heretofore known and/or utilized (see U.S. Pat. Nos. 3,430,688 and 3,289,748). In at least one case, such a garment has been used with a liquid oxygen converting system to provide an integrated cooling and breathing system (see U.S. Pat. No. 4,024,730).

While the integrated system above described may be effective in some applications, such system fails to provided a compact unit (capable of being carried on one's body) such as might be required by fire fighters or other mobile personnel needing such a system. Such systems require electrical input (undesirable in gaseous environments), rely on manual activation to control flow rates and thus cooling, and make no use of heat exchange to control system operational parameters other than temperature of the breathable air. Moreover, the oxygen converting systems used therein suffer many of the same drawbacks as heretofore discussed. Further improvement could thus be utilized.

SUMMARY OF THE INVENTION

This invention provides a body cooling system and method which both cools the body of a user while conditioning a mixed gas for end use, the mixed gas used for heat exchange with a fluid to cool the body. The system is lightweight and adapted for use with an apparatus for storing mixed gas received at cryogenic temperature and supercritical pressure and delivering the mixed gas at a non-cryogenic temperature to a utilization fixture, such as a breathing mask in the case of air or a torch or engine in the case of other mixed gasses. The system requires no electrical input, requires no manual manipulation to control cooling fluid flow rates, and makes use of heat exchange for body cooling to control system operational parameters including temperature of the usable gas and maintenance of remaining stored gas in a single phase.

The apparatus includes a containment vessel having an outlet for selective expulsion of the mixed gas from the containment vessel to the body cooling system and, ultimately, the utilization fixture. A passive heat exchanger is provided at the containment vessel for receiving mixed gas expelled through the outlet to the body cooling system and routing the mixed gas at the containment vessel to introduce sufficient heat into the containment vessel so that the mixed gas remaining in the containment vessel is in a single phase.

The body cooling system includes a fluid circulation network incorporated into a garment worn on a body to be cooled and a first heat exchanger connectable between the outlet and the heat exchanger of the containment vessel and routed for heat exchange between mixed gas received through the outlet and fluid at the fluid circulation network. A second heat exchanger is connectable between the heat exchanger of the containment vessel and the utilization fixture and routed for heat exchange between mixed gas received from the containment vessel heat exchanger and fluid at the fluid circulation network.

The system may also include another, selectively actuatable, heat exchanger network for selectively controlling cooling level of fluid at the fluid circulation network. A pneumatic pump is connected with the fluid circulation network and between the outlet of the containment vessel and the utilization fixture, the pump utilizing the gas being delivered to the fixture from the containment vessel for moving fluid through the fluid circulation network. The pump is preferably a variable rate pump for moving fluid through the fluid circulation network at a variable rate determined by sensed work rate of a user wearing the garment (for example, rate of use of the gas in the case of breathable air).

The method for storing and delivering mixed gas to provide both body cooling and conditioning of the mixed gas for use includes the steps of loading cryogenic temperature mixed gas into a container, selectively expelling the mixed gas from the container, circulating fluid around a body at a rate determined by sensed work rate of the body, and exchanging heat between the circulating fluid and the expelled mixed gas to cool the circulating fluid to thus cool the body and to warm the expelled mixed gas for use thereof.

It is therefore an object of this invention to provide an improved body cooling system and method.

It is another object of this invention to provide an improved integrated body cooling and mixed gas conditioning system and method.

It is another object of this invention to provide an improved body cooling system and method which both cools the body of a user while conditioning a mixed gas used for heat exchange with a fluid to cool the body for end use.

It is still another object of this invention to provide a lightweight body cooling system adapted for use with an apparatus for storing mixed gas received at cryogenic temperature and supercritical pressure and delivering the mixed gas at a non-cryogenic temperature to a utilization fixture, such as a breathing mask in the case of air or a torch or engine in the case of other mixed gasses.

It is another object of this invention to provide a body cooling system and method which requires no electrical input for heating or cooling.

It is yet another object of this invention to provide a body cooling system and method which requires no manual manipulation to control cooling fluid flow rates.

It is still another object of this invention to provide a body cooling system and method for use with a cryogenic mixed gas storage and delivery apparatus which makes use of heat exchange for body cooling to control apparatus operational parameters including temperature of the usable gas and maintenance of remaining stored gas in a single phase.

It is another object of this invention to provide a body cooling system adapted for use with an apparatus for storing mixed gas received at cryogenic temperature and delivering the mixed gas at a non-cryogenic temperature to a utilization fixture, the apparatus including a containment vessel for receiving the mixed gas at cryogenic temperature and having an outlet for selective expulsion of the mixed gas from the containment vessel therethrough to said body cooling system, the vessel having a passive heat exchanger for receiving mixed gas expelled through the outlet to the body cooling system and routing the mixed gas at the containment vessel to introduce sufficient heat into the containment vessel so that the mixed gas remaining in the containment vessel is in a single phase, the system including a fluid circulation network incorporated into a suit worn on a body to be cooled, a first heat exchanger connectable between the outlet and the heat exchanger of the containment vessel and routed for heat exchange between mixed gas received through the outlet and fluid at the fluid circulation network, and a second heat exchanger connectable between the heat exchanger of the containment vessel and the utilization fixture and routed for heat exchange between mixed gas received from the containment vessel heat exchanger and fluid at the fluid circulation network.

It is another object of this invention to provide a body cooling system which includes, in combination with passive heat exchangers, a selectively actuateable heat exchanger for enhancing control of cooling level of cooling liquid used in a fluid circulation network of a garment.

It is still another object of this invention to provide a body cooling system utilizing a pneumatic pump connected with a body cooling fluid circulation network and between an outlet of a cryogenic air containment vessel and a breathing unit, the pump utilizing the air being delivered to the breathing unit from the containment vessel for moving fluid through the fluid circulation network.

It is yet another object of this invention to provide an air storage and delivery system providing both body cooling and breathable air to a user that includes a pressure vessel for containing air received at cryogenic temperature and at a pressure so that the air in said vessel is in a single phase, the vessel having an outlet, a breathing unit, a garment having a fluid circulation network, a first heat exchanger connected between the outlet from the pressure vessel and the breathing unit for receiving air from the pressure vessel through the outlet and conducting the air for heat exchange with fluid in the fluid circulation network of the garment to both cool fluid in the fluid circulation network and warm the air for use at the breathing unit, and a variable rate pump for moving fluid through the fluid circulation network at a variable rate determined by rate of use of air through the breathing unit.

It is still another object of this invention to provide a method for storing and delivering mixed gas to provide both body cooling and conditioning of the mixed gas for use which includes the steps of loading cryogenic temperature mixed gas into a container, selectively expelling the mixed gas from the container, circulating fluid around a body at a rate determined by sensed work rate of the body, and exchanging heat between the circulating fluid and the expelled mixed gas to cool the circulating fluid to thus cool the body and to warm the expelled mixed gas for use thereof.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a perspective view of the fluid storage and delivery apparatus used in this invention;

FIG. 2 is a schematic diagram of the apparatus of FIG. 1;

FIG. 11 is a diagram illustrating operation of the loading apparatus of FIG. 9;

FIG. 12 is a rear view of a carriage and conditioning unit used with the apparatus of FIG. 1;

DESCRIPTION OF THE INVENTION

Figure 3:
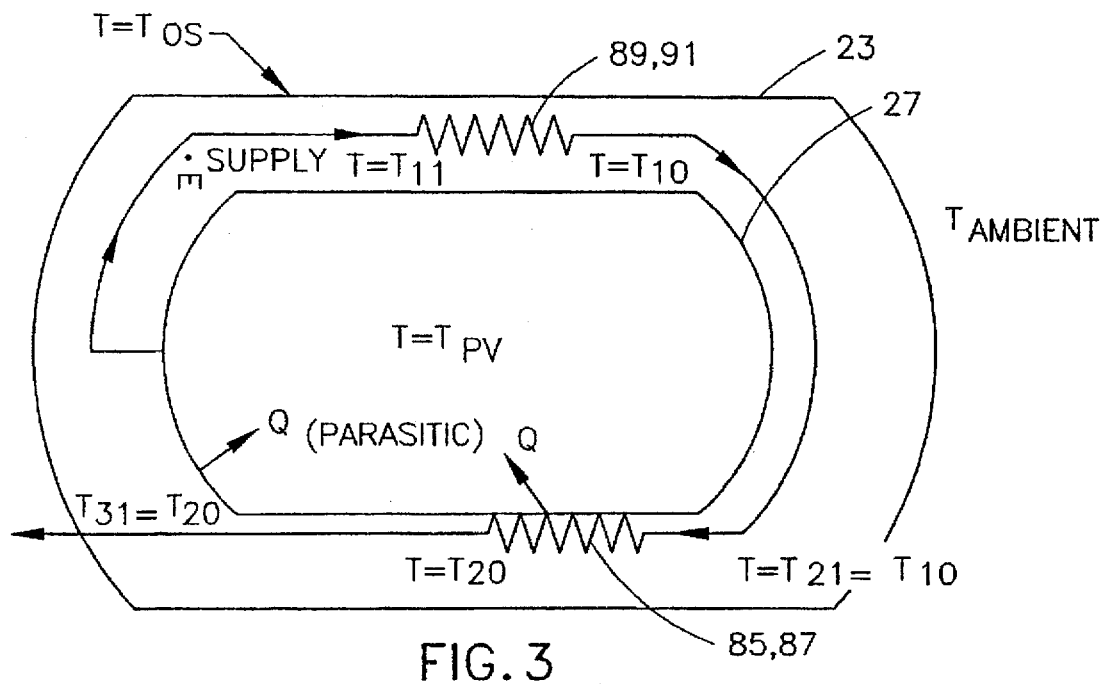
FIG. 3 is a diagrammatic illustration of heat exchange in the apparatus of FIG. 1.

Storage and delivery apparatus 21 (incorporated into, or used in association with, this invention) is shown in FIG. 1 for containing supercritical pressure cryogenic air as a breathing supply to thus obviate the problems of oxygen enrichment and attitude dependence of a liquid air breathing bottle. The use of a supercritical cryogenic fluid state for the air provides a gas which is in a single phase, high density condition and which can be withdrawn from any location in the apparatus which may itself be in any attitude. Supercritical pressure is required so that the air at cryogenic temperature will exhibit no two phase characteristics.

While an air delivery apparatus will be described and referred to herein, it should be understood that the apparatus could as well be used for any fluid delivery to a utilization fixture, for example elemental and/or compound gasses, or, most particularly, mixed gasses such as air (nitrogen-oxygen), helium-oxygen, argon-oxygen, helium-argon, methane-hydrogen, or the like where prevention of separation of the components due to gravitational effects and/or due to frictional separation from boiling of a liquid is desired.

The critical pressure for air is 37.25 atm. (547.37 psia) and the critical temperature is 132.5K (238.54° R). The colder the initial temperature of the air (preferably down to 140° R) and to a much lesser extent the higher the pressure (preferably in a range between 750 psia and 2,000 psia), the greater will be the storage density and thus the ability to provide significant rated use times while utilizing smaller, lighter storage units.

The use of supercritical fluid also provides a standby storage advantage over liquid in that energy required to expel a pound of fluid in the single phase storage condition is greater than that required to boil-off a pound of liquid and expel the vapor (161.68 Btu/Lbm at 750 psia versus 86.67 Btu/Lbm at one atmosphere, respectively). Supercritical air may thus be stored for longer times before reservicing than liquid air.

As shown in FIGS. 1 and/or 2, apparatus 21 includes outer shell, or vacuum jacket, 23, protective head 25 (for example, a one-piece cast aluminum head) sealed to shell 23 and pressure vessel 27 within shell 23 for containing the air. Fill line 29 passes through shell 23 and vessel 27 at inlet 31 for filling and/or refilling as hereinafter set forth (all connections and passages with, to and from vessel 27 and shell 23 set forth herein being formed by means known to those skilled in the pertinent art). Passive heat exchange and fluid transport system 33 is connected to vessel 27 at outlet 35 for conducting air expelled from vessel 27 to a use destination (for example to the carriage and conditioning unit hereinafter described).

Insulation 37 fills, and is vacuum jacketed within, space 39 between vessel 27 and shell 23 and can be, for example, formed of ten layers of multi-layered insulation consisting of double aluminized MYLAR spaced with tissue glass (a borosilicate fiber paper) or polyester netting. Fins 41 (in one embodiment being about four inches wide by 0.083 inch thick aluminum fins) are welded to, or formed integrally with (though they could also be remote from the shell), shell 23 for effectively increasing the surface area of the shell exposed to ambient temperature air to enhance heat exchange as discussed in more detail hereinbelow.

Vent line 43 is connected with vessel 27 for relief venting through relief valve 45 and to maintain pressure during standby and during filling. Relief valve 45 should include a TEFLON seal and be rated for cryogenic temperatures, and as illustrated is preferably biased at atmospheric pressure for relieving top pressure and thus reducing pressure through transport system 33 without waste of fluid. Relief valve 47 is employed as a final high reliability safety device, and should be sized to relieve at approximately 10% (approximately 200 psi) above relief pressure of valve 45.

Flow control valves 49, 51 and 53 are manual valves for control of filling, draining and use of apparatus 21, and may be bellows type valves of all welded construction designed for temperature cycling applications, and/or may be combined into one or more operational units. Quick disconnects 55, 57, and 59 are provided for making required connections to a loading apparatus (for example, as hereinafter described) or carriage and conditioning unit.

Pressure gauge 61, for example a small bourdon tube pressure gauge, is used for checking tank pressure, and quantity sensor 63 having readout 65 monitors fluid quantity in vessel 27 (for example, using a capacitance probe to measure the dielectric constant which varies from approximately 1.4 in the full condition to 1.0 in the empty condition). An audible alarm can be provided to alert a user when the fluid quantity reaches a selected low level, all electronics being powered, for example, by a 9 volt battery.

Pressure regulator 67 is a back-pressure regulator used, in conjunction with valve 51, to maintain pressure during standby and filling operations. As shown in FIG. 2, line 43 may be couplable through valve 45 with conditioning unit 69 at carriage and conditioning unit 71 using quick disconnect 73 so that air expelled therethrough may be used in the system.

Conditioning unit 69 includes heat exchanger 75 for heating expelled air to a breathable temperature, pressure regulator 77, optional flowmeter 79 and quick disconnect 81 for connection with a utilization device such as a mask.

Configuration of the various components varies with operation. During storage, valves 49 and 53 and quick disconnects 55, 57 and 81 are all closed. During loading operations valves 49 and 51, quick disconnects 55 and 59 and pressure regulator 67 are operational. During standby, valve 51, quick disconnect 59 and pressure regulator 67 remain open, while in operation valve 51, quick disconnect 59 and pressure regulator 67 are closed, and valve 53 is opened.

Vessel 27, in one particularly useful embodiment, has a volume of less than 4.2 liters (preferably about 4 liters), the apparatus having an overall diameter of about five inches, length of about 22 inches, operating pressure of 1,600 psia, and weight empty of about 10.7 pounds (filled weight of about 19 pounds) for a rated delivery time of about one hour ("rated delivery" herein refers to NIOSH rating of 40 SLM (standard liters per minute) for breathing apparatus, equating to about 6.7 lbs. of air per hour of delivery). In such case, vessel 27 is made of titanium, though other materials could be used.

By way of further example, for a rated time of two hours at the same operating pressure, the apparatus having a titanium vessel 27 weighs under 30 pounds filled, has a vessel volume of about 7.2 liters, a diameter of 6.5 inches and a length of about 25 inches.

Figure 4:
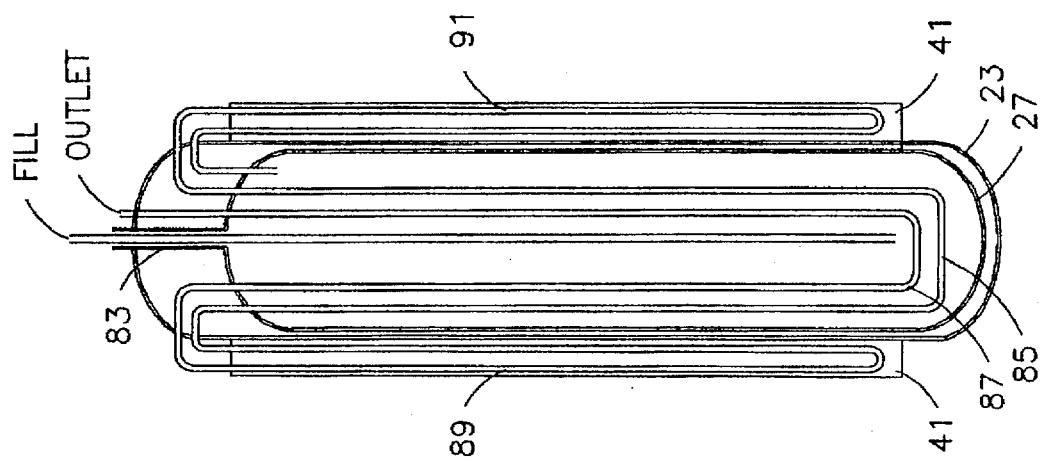
FIG. 4 is a diagrammatic sectional illustration of the storage and delivery apparatus of FIG. 1.

Apparatus weight depends on vessel 27 volume, operating pressure and materials. Pressure vessel and outer shell materials could include composites such as FIBERGLASS, KEVLAR or graphite. Metals that could be used include stainless steel, aluminum, INCONEL or titanium. Aluminum or composite pressure vessels would require bimetal joints, with a composite vessel 27 possibly including an aluminum liner and neck plug 83 (shown in FIG. 4 for housing inlet and outlet plumbing and for, in part, positioning vessel 27 in shell 23) overlaid with an S-glass/epoxy composite (a composite fabric heretofore used in aerospace applications). The advantage in weight of such construction is significant, with a 4 liter apparatus (rated use exceeding 60 minutes) having a diameter of 4.5 inches and a vessel weight of less than four pounds. Overall, weights for a 4 liter apparatus range from about 10.7 to 16.4 pounds at an operating pressure of 1,600 psig, the lightest having a titanium, Inconel 718 or aluminum (6061-T6 welded and heat treated with a burst pressure in excess of 6,000 psig) vessel 27 with an aluminum shell 23.

Figure 7:
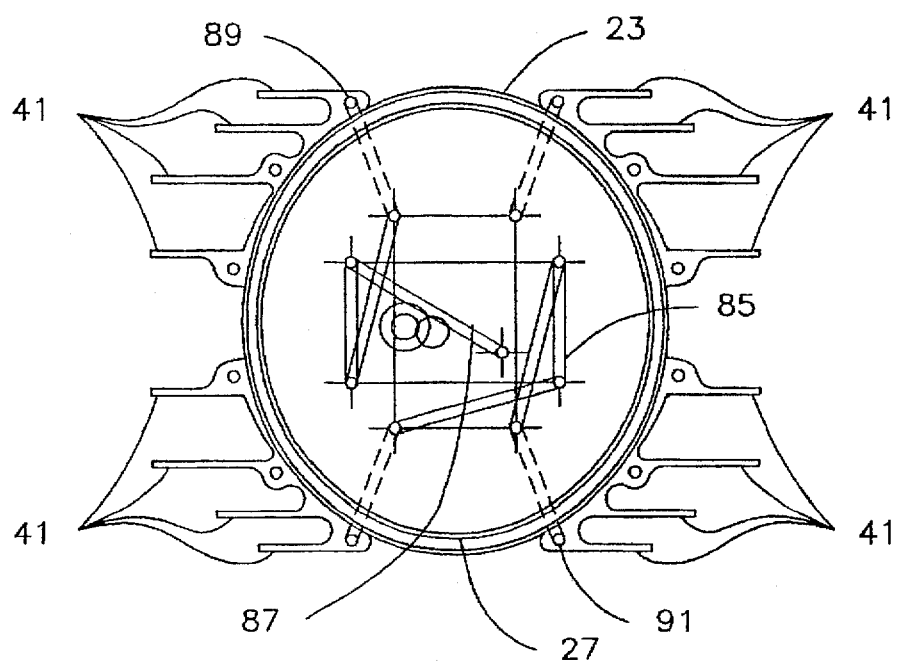
FIG. 7 is a sectional view taken through section line 7—7 of FIG. 6.
Figure 6:
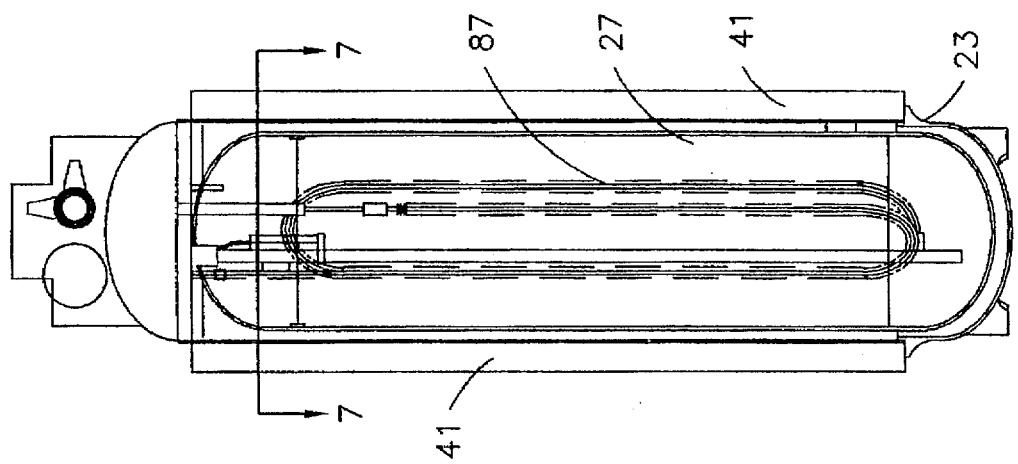
FIG. 6 is a sectional view illustrating part of the inner routed portion of the heat exchanger of the storage and delivery apparatus of FIG. 1.
Figure 5:
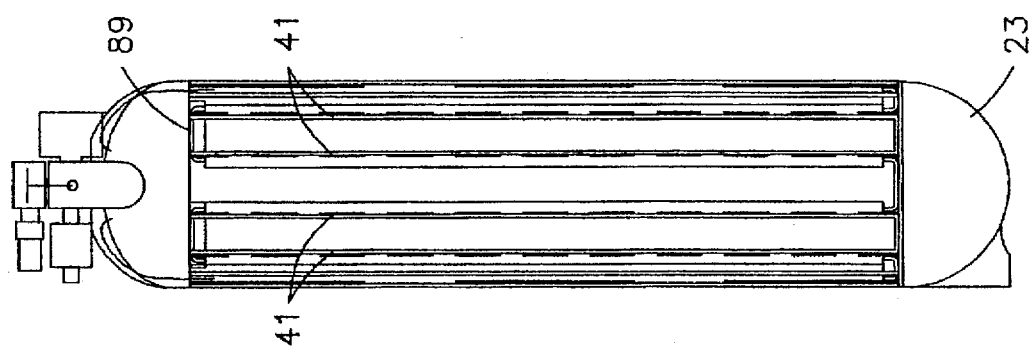
FIG. 5 is a side view of the outer routed portion of the heat exchanger of the storage and delivery apparatus of FIG. 1.

Referring now to FIGS. 2 and 3, passive heat exchange system 33 is a double loop heat exchange system (a single loop system could be used in a system as hereinafter set forth) including inner exchange loop portions 85 and 87 connected either to the outer part of vessel 27 or passing into vessel 27 in direct contact with fluid therein. Outer exchange loop portions 89 and 91 are connected with shell 23 or fins 41 or could be made integral to fins 41 as shown in FIG. 7. The heat exchange loop portions are preferably constructed of ⅛" diameter aluminum tubing, though other materials could be utilized.

Sufficient heat must be efficiently transported from outer shell 23 to pressure vessel 27 to maintain the gas in the vessel in the single phase and to provide expulsion energy for delivery of the gas from the vessel. A design to provide adequate heat transfer for expulsion must recognize that the process is a transient one. Fluid conditions and properties constantly change throughout the entire expulsion process.

For example, the expulsion energy for supercritical air ranges from approximately 35 BTU/Lbm to 160 BTU/Lbm in the pressure and temperature range of interest, with the integrated average expulsion energy being approximately 65 BTU/Lbm. Since heat leak through plumbing and other fixtures alone is insignificant compared to that required to expel the air needed (only about 9.0 BTU/Hr for a shell temperature of 530° R and a vessel temperature of 180° R) for use by an individual user at maximum exertion (estimated to be about 16.0 lbm/hr), mass flow heat exchange system 33 must be calculated to deliver sufficient heat for operation of the apparatus.

An example demonstrating heat transfer requirement for a single point in the expulsion process follows. As illustrated by FIG. 3, expelled tank fluid passes through heat exchangers 89/91 increasing its temperature to nearly that of the surface of outer shell 23 (preferably by free convection to the ambient air though various means of forced convection of ambient air to shell 23 could be utilized to provide more energy exchange). The fluid then flows to heat exchangers 85/87, respectively, cooling the fluid and dumping heat for fluid expulsion and single phase maintenance into fluid remaining in pressure vessel 27. The maximum amount of heat (Q) that can be transported from shell 23 to vessel 27 depends on the mass flow rate of outflowing fluid ($m_{supply}$), the specific heat of the cryogenic air ($C_p$), and the temperature difference between shell 23 and vessel 27 as in the following equation:

$$Q = m_{supply} C_p (T_s - T_v)$$

Since the $C_p$ of cryogenic air varies with temperature, a more accurate representation of the heat transported is:

$$Q = m_{supply}(h_s - h_v)$$

where $h_s$ is the enthalpy of air at the outer shell temperature and fluid pressure and $h_v$ is the enthalpy of air at the pressure vessel temperature and fluid pressure.

A realistic number for heat exchanger efficiency is considered to be 0.90, so that the Q calculated above would be multiplied by this efficiency twice (for external and internal heat exchangers) to obtain a heat flux for the heat exchanger described. Assuming a nominal fluid pressure of 800 psia, an ambient temperature of 530° R ($h_s$=122 BTU/Lbm) and pressure vessel fluid temperature of 150° R ($h_v$=−48 BTU/Lbm), the total Q transferred to the pressure vessel fluid is $$Q = (0.9)(0.9)16.0 \; Lbm/Hr(122-(-48))BTU/Lbm \; Q=2200 \; BTU/Hr$$

Taking these numbers into consideration as well as the required increase in temperature of vessel 27, a double loop exchange system as shown would be required to achieve approximately 2480 Btu/hr that will drive 16 lbm/hr out of vessel 27 while remaining single phase.

In order to predict the amount of heat transfer between the outer shell and ambient air, a free convection correlation for a long horizontal cylinder geometry is utilized so that heat transfer by free convection, $q_{conv}$, from ambient air to shell 23 is given by:

$$q_{conv} = h \pi D L (T_S - T_\infty)$$

where h equals the average free convection film coefficient, D equals cylinder diameter, L equals cylinder length, $T_S$ equals cylinder temperature, and $T\infty$ equals ambient air temperature. The free convection film coefficient may be obtained from the dimensionless Rayleigh number, Ra, by:

$$Ra = g\beta(T_S - T\infty)L^3/\alpha v$$

where g equals acceleration of gravity, β equals the volume coefficient of expansion, α equals thermal diffusivity, and v equals dynamic viscosity.

In the case at hand, solution for Ra yields 1.4×10⁹. An appropriate correlation for the Nusselt number, Nu, is:

$$Nu_D = 0.10(Ra)^{1/3}$$

which for this example is equal to approximately 110.0. The film coefficient is related to the Nusselt number by:

$$h=(Nu\ k)/L$$

where the thermal conductivity, k, for air at the average air temperature is 0.013 BTU/Hr-Ft-°F. This results in an average film coefficient, h, of 0.95 BTU/Hr-Ft$^2$-°F.

Thus, for an outer shell area of approximately 2.5 ft$^2$, an ambient temperature of 530° R and average shell temperature of 300° R, the total amount of heat available from free convection will be 550 BTU/Hr. Therefore, a higher product of film coefficient and outer shell 23 surface area is required in order to transfer adequate heat to vessel 27 to maintain desired pressure. Since the free convection heat transfer coefficient is fixed due to geometry and fluid conditions, the only method to increase this product in the embodiment of apparatus 21 shown in FIG. 1 is to effectively increase the surface area of shell 23 as is done utilizing fins 41.

Figure 8:
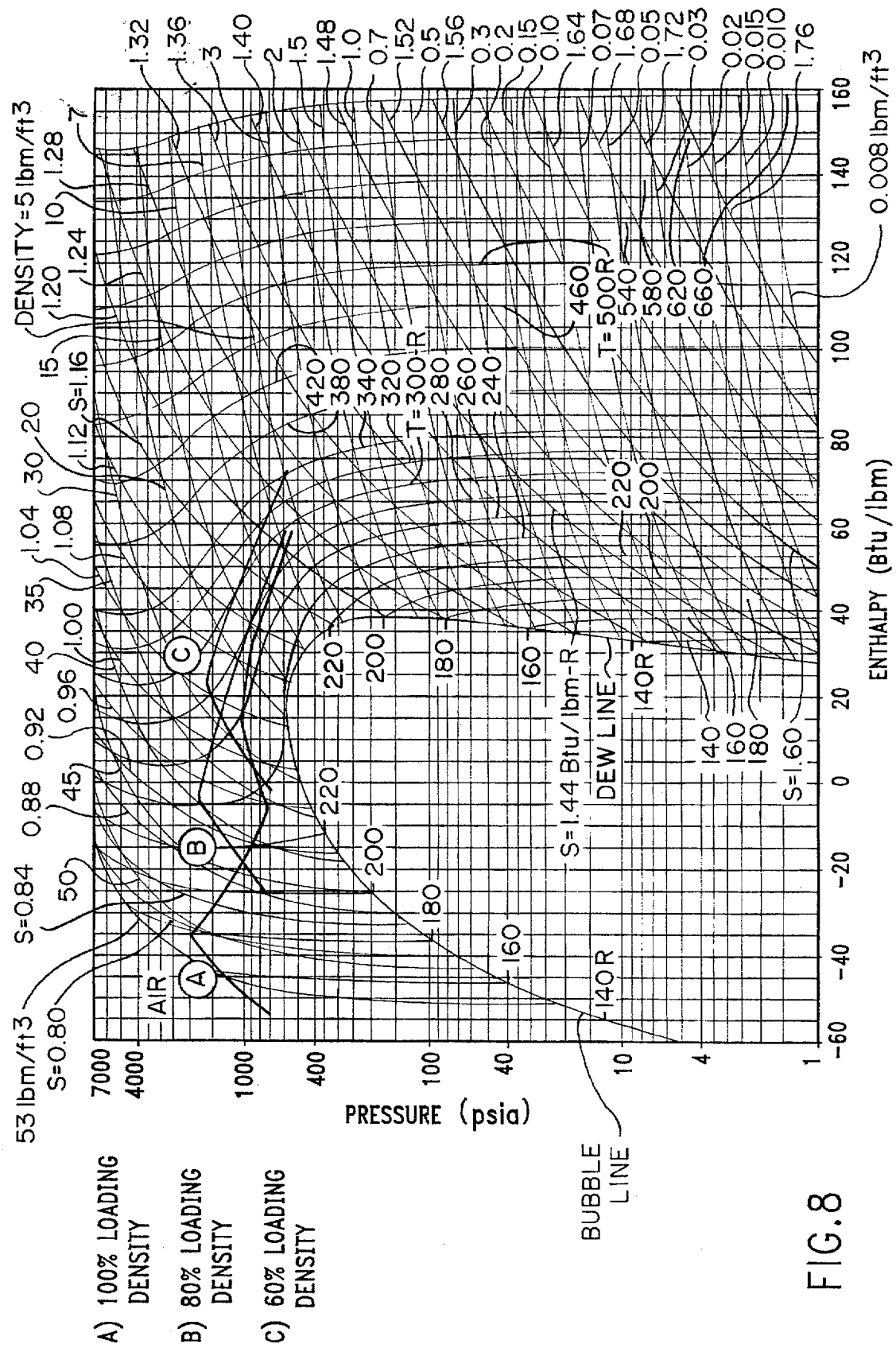
FIG. 8 is a Mollier chart showing performance of the apparatus of FIG. 1 under a variety of loading densities.

FIGS. 4 through 7 show routing of the heat exchange loop portions as suggested hereinabove. For a 3 liter tank design, 63-64 feet total of tubing is utilized for heat exchange system 33. FIG. 8 is a Mollier chart having plotted thereon results of various tests illustrating an adequate degree of separation of the transient fluid condition from the two-phase region utilizing the apparatus of this invention.

While not illustrated herein, vessel 27 is preferably supported in shell 23 on neck tube support 83 attached to both vessel 27 and shell 23. Bumpers, or pads, would be desirable adjacent to the lower, unsupported, end of vessel 27 to thwart movement of vessel 27 in excess of maximum allowable stress to neck 83 or its connections to vessel 27 and shell 23.

Figure 10:
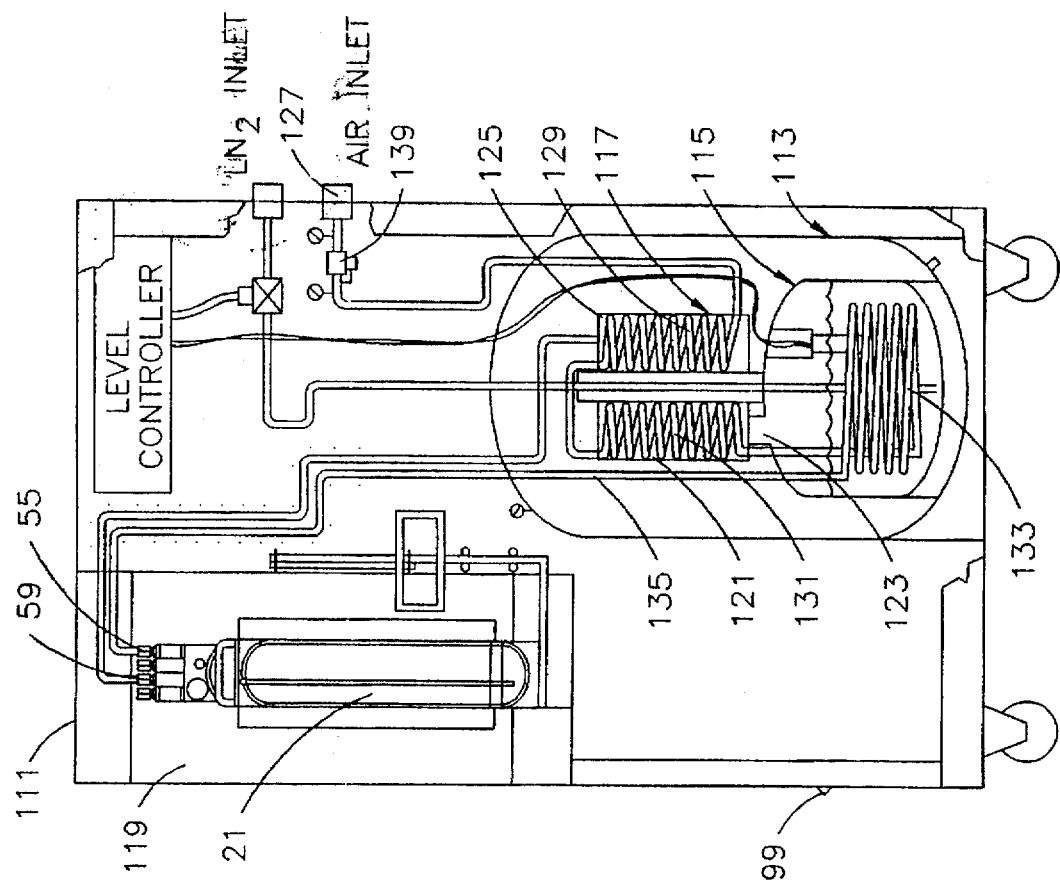
FIG. 10 is a schematic sectional view of the loading apparatus of FIG. 9.
Figure 9:
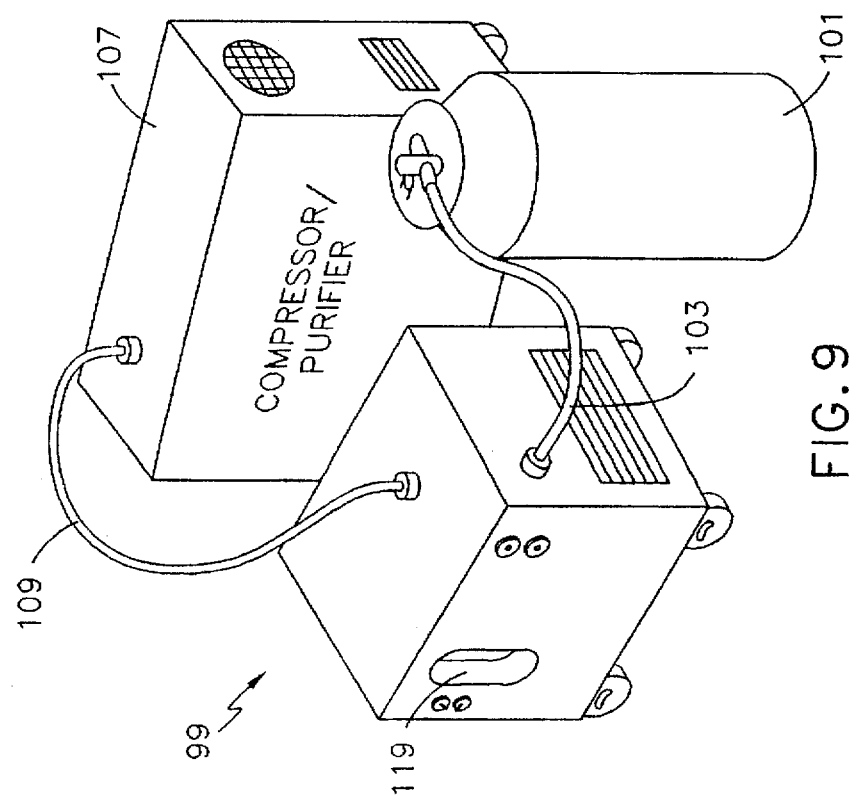
FIG. 9 is a perspective view of a loading apparatus for loading fluid into the storage apparatus.

FIGS. 9 through 11 illustrate a loading apparatus 99 usable with this invention, advantageous in that loading at supercritical pressure is made possible (it being understood that any loading method for placing the cryogenic gas in vessel 27 could be utilized with the body cooling system of this invention as hereinafter set forth). Apparatus 99 has coolant (such as LN$_2$, i.e., liquid nitrogen) supply 101 connected thereto by supply conduit 103 (an LN$_2$ refrigerator or other means could be utilized). Air supply 107 is connected to apparatus 99 by conduit 109 (a compressor being illustrated, though a high pressure compressed air bottle could also be utilized). An alternative fill apparatus could be provided which utilizes a source of cryogenic temperature air itself maintained at supercritical pressure, in which case, loading would be simplified even if possibly more expensive and unwieldy. Apparatus 99 includes housing 111, vacuum chamber 113 having LN$_2$ bath chamber 115 and precooling chamber 117 therein, and storage apparatus insertion chamber 119 for receipt thereinto of a storage apparatus to be serviced (preferably having a self aligning load, securing and quick disconnect mechanism for ease of use by an operator). Precooling chamber 117 includes heat exchange chamber 121 connected with boil-off line 123 and chamber 125 connected with fill vent quick disconnect 59 from apparatus 21 to provide preliminary cooling (from about 20° C. to about −60° C.) of air received through inlet 127 from supply 107.

Exchange coils 129 and 131 are positioned in chambers 125 and 121, respectively, air flowing in the coils then being passed through LN$_2$ bath in coil 133 of conduit 135 (it should be recognized that mechanical refrigeration could also be utilized) to lower temperature of the air to about −195° C. The air is then received in apparatus 21 through quick disconnect 55. Since the air from supply 107 is received at loading apparatus 99 at or above the critical pressure (about 800 psi), the fluid is received at apparatus 21 in the single phase condition, thus rendering apparatus 21 usable substantially immediately after filling. Where supply compressor unit 107 is utilized rather than a high pressure gas bottle containing high purity air, filter/dryer/CO$_2$ scrubber 137 and pressure regulator 139 are provided. Compressor supply unit 107 may include for example, an oil-free 1,000 psi compressor. Various gauges, readouts, program controls and the like could be utilized to enhance ease of operation and safety of the apparatus.

Figure 13:
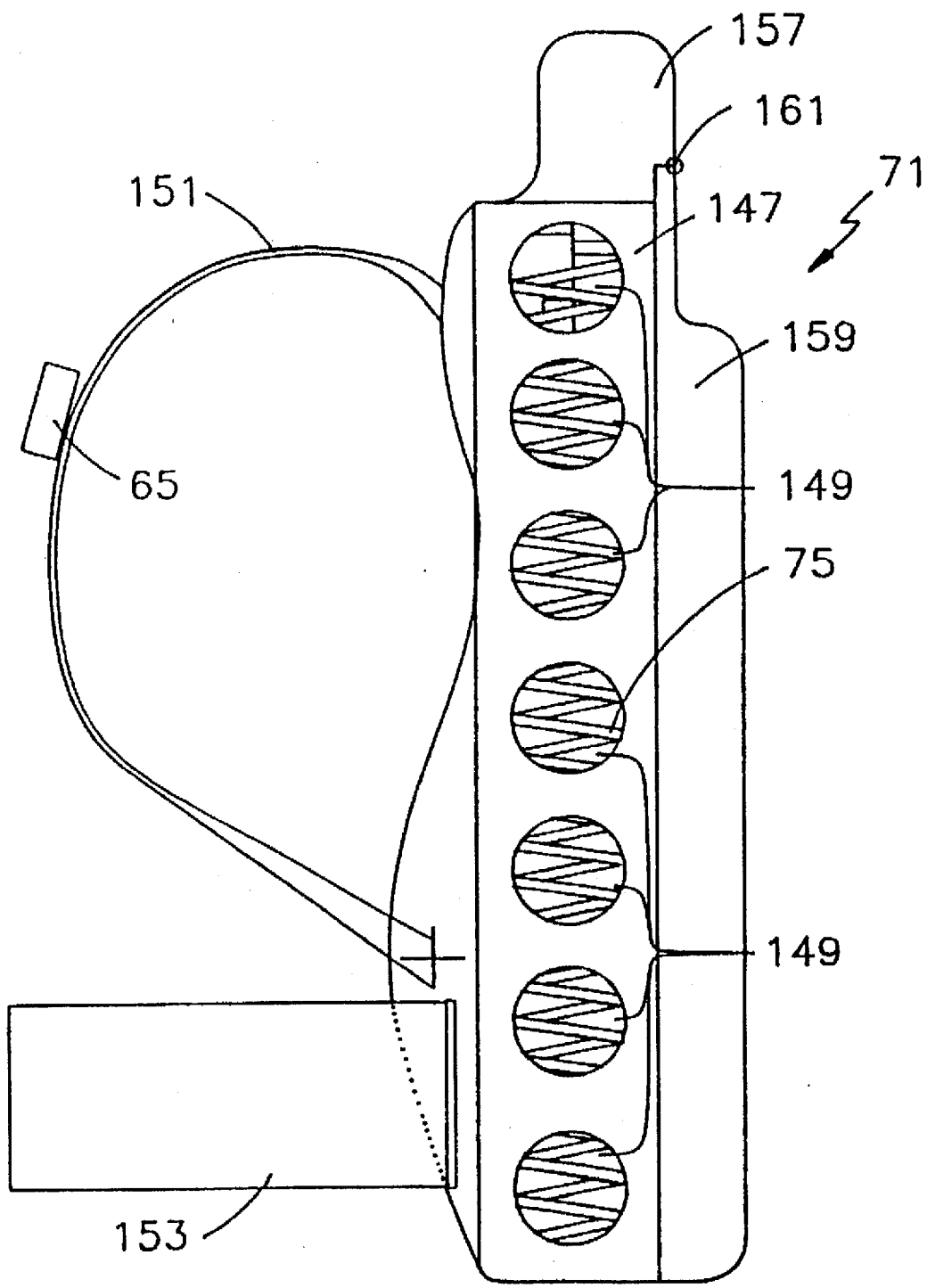
FIG. 13 is a side view of the unit of FIG. 12.

FIGS. 12 and 13 illustrate carriage and conditioning unit 71 utilizable with this invention. Unit 71 includes pack structure 147 made, for example, of high strength, light weight molded plastic. Structure 147 has a plurality of openings 149 therein to assure proper flow of ambient air around apparatus 21 and the various heat exchangers mounted therein (for example heat exchanger 75, though the openings will serve the same function for other exchangers as hereinafter set forth). Air conditioning heat exchangers 75 and pressure regulator 77 are mounted on structure 147 by any convenient means, and adjustable harness 151 and waist belt 153 are mounted in selected sets of receiving slots at the back of the pack structure. Remote fluid quantity readout 65 may be attached to harness 151 for ease of observation. Apparatus 21 is snugly maintained in structure 147 by molded head 157 and hinged door 159 connected at hinge 161.

Figure 14:
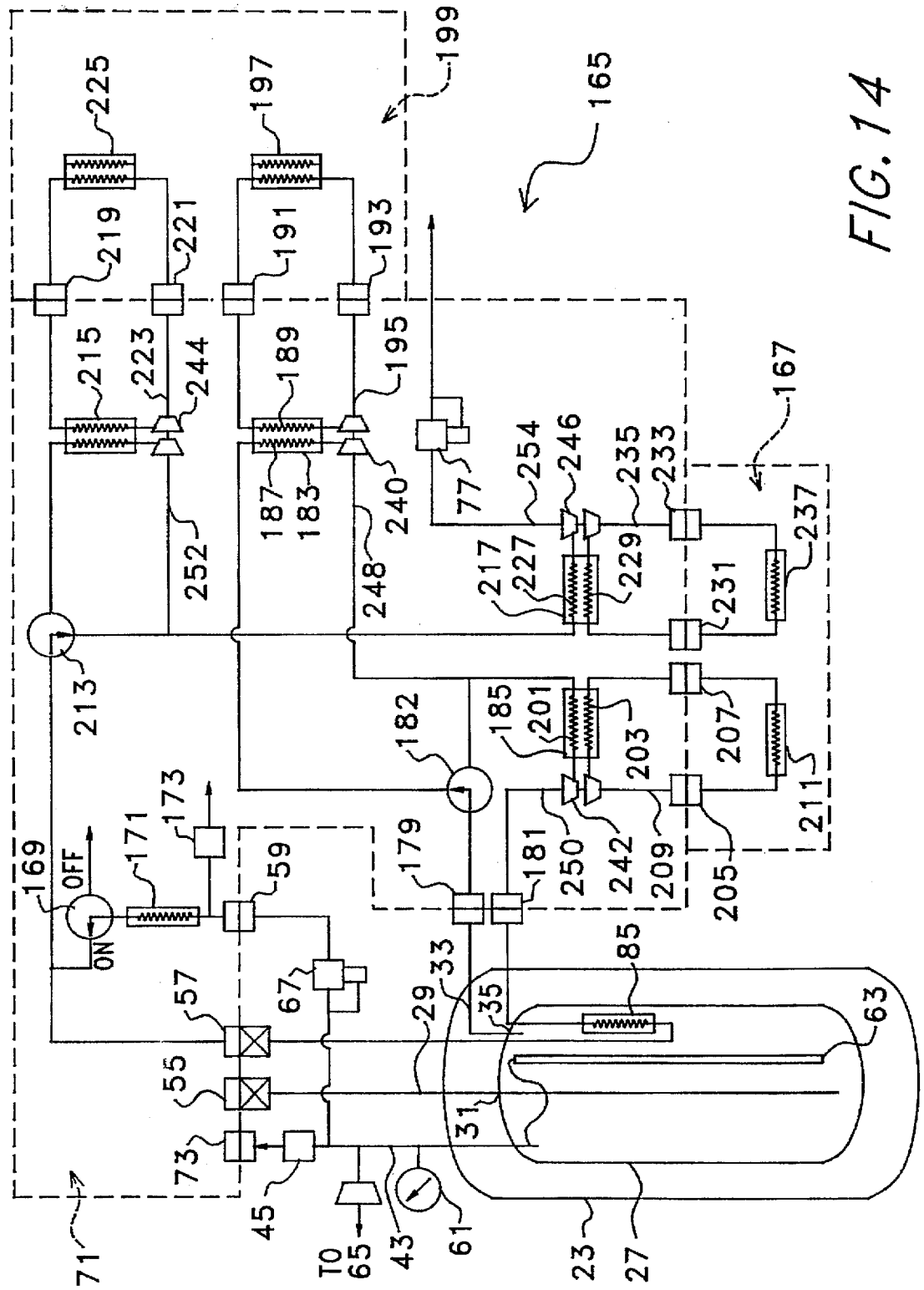
FIG. 14 is a schematic illustration of the body cooling system of this invention used in association with a modified apparatus of FIG. 2.
Figure 15:
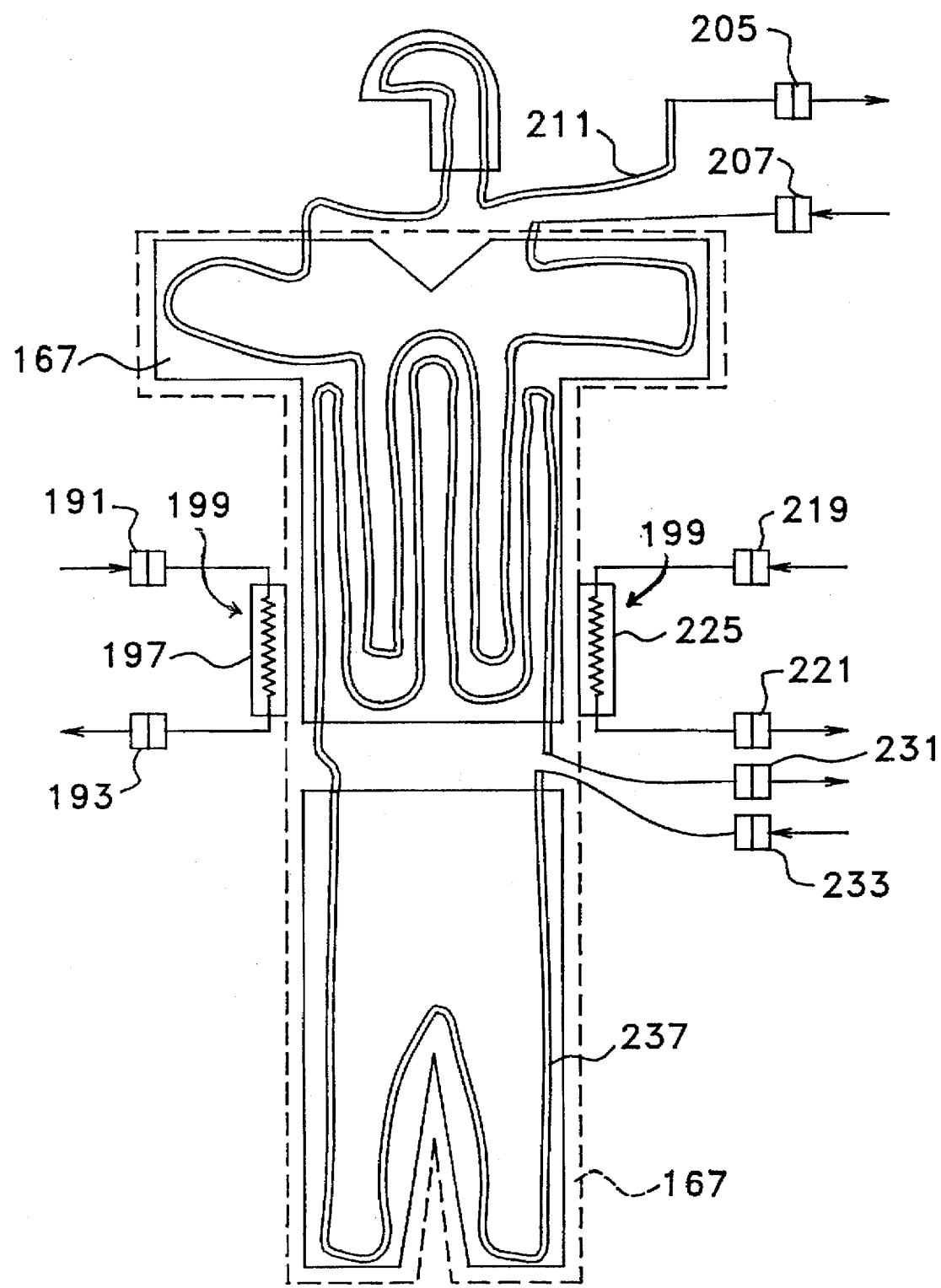
FIG. 15 is a schematic illustration of a fluid circulation network incorporated into a garment for use in the system of FIG. 14.

Turning now to FIGS. 14 and 15 illustrating a first embodiment of body cooling system 165 of this invention, many of the features of apparatus 21 as shown in FIG. 2 remain substantially the same for use with the system, including outer shell 23 having an insulated pressure vessel 27 therein, various outlets 31 and 35, lines 29, 33 and 43, quick disconnects 55, 57, 59 and 73, relief valve 45, pressure regulators 67 and 77, and pressure and quantity gauges and readout 61, 63 and 65. However, only one internal heat exchange loop 85 is required for maintaining cryogenic gas in vessel 27 in a single phase and providing sufficient expulsion pressure since heat input is no longer provided by exchange with the ambient atmosphere (formerly at exchange loops 89 and 91 at fins 41 and shell 23 in FIG. 2), but by heat exchange with fluid heated by the body of a wearer of garment 167.

Quick disconnect 59 is now connected at carriage unit 71 to valve 169 through passive heat exchanger 171 for recycling of gas expelled thereat into the system when valve 169 is on. Valve 169 is off when the unit is not connected at carriage unit 71 and in a standby condition. Relief valve 173 is provided to maintain desired pressure (for relief at about 1,000 psi). Heat exchanger 171 is situated to pre-warm gas before passage through valve 169 to prevent valve damage and thus leaking.

Quick disconnects 179 and 181 are provided for interconnection of vessel 27 at carriage unit 71 with system 165. Mixed gas expelled at outlet 35 through line 33 first reaches control valve 182 where the gas is directed either to pre-warming heat exchanger 183 or directly to body cooling heat exchanger 185, depending on valve setting. Pre-warming heat exchanger 183 includes gas conduit 187 in heat exchange relationship with fluid conduit 189. Fluid conduit 189 is connected by disconnects 191 and 193 into a discrete fluid (water or water and antifreeze) circulation loop 195 including heat exchanger 197 located in an outer protective garment 199 worn over garment 167 for heat exchange with the ambient atmosphere. Gas at conduit 187 is thus warmed (for air, from approximately −160° C. to about −30° to 15°

C.) before it reaches heat exchanger 185, pre-warming being necessary in some circumstances to prevent over cooling of the user's body.

Body cooling heat exchange and heat exchange for heat input to vessel 27 at heat exchange loop 85 is accomplished at exchanger 185 including gas conduit 201 in heat exchange relationship with fluid conduit 203. Fluid conduit 203 is connected by disconnects 205 and 207 into a discrete fluid circulation loop 209 including heat exchange network (a fluid circulation network in garment 167, as also shown in FIG. 15).

Where pre-warming is not required under the circumstances, valve 182 directs the mixed gas to heat exchanger 185 (in the case of air, at a temperature of about −160° C.) for heat exchange with fluid in loop 209, preferably lowering fluid temperature to no lower than about 10° C., for example, in the case of water or water and antifreeze, and raising the temperature of the gas, for example to about 20° C. in the case of air where fluid circulating in loop 209 is raised in temperature by the user's body at exchange network 211 to about 30° C. Where the gas has been pre-warmed, since gas entering exchanger 185 is of a higher temperature, the overall body cooling effect is controlled (i.e., fluid temperature at network 211 is controlled). The warmed gas is then directed to heat exchange loop 85 through disconnect 181, providing energy as heretofore discussed at vessel 27.

Gas exiting exchange loop 85, again cooled to about −160° C. in the case of air, is presented through quick disconnect 57 at control valve 213 where the gas is directed either to pre-warming heat exchanger 215 or directly to body cooling heat exchanger 217, depending on valve setting. Pre-warming heat exchanger 215 serves the same purpose for exchanger 217 as heretofore described for exchangers 183 and 185, and is similarly arranged for heat exchange, utilizing quick disconnects 219 and 221 to provide fluid circulation loop 223 having external heat exchanger 225.

Body cooling heat exchange and heat exchange to condition gas for use (formerly provided at heat exchanger 75 in FIG. 2), for example to raise the temperature of cryogenic air to a breathable temperature, are accomplished at heat exchanger 217 including gas conduit 227 in heat exchange relationship with fluid conduit 229. Fluid conduit 229 is connected by disconnects 231 and 233 into a discrete fluid circulation loop 235 including heat exchange network 237, a fluid circulation network in garment 167.

Where pre-warming is not required under the circumstances, valve 213 directs the mixed gas to heat exchanger 217 (in the case of air at a temperature of about −160° C.) for heat exchange with fluid in loop 235, preferably lowering fluid temperature to no lower than about 10° C., for example, in the case of water or water and antifreeze, and raising the temperature of the gas, for example to about 20° C. in the case of air where fluid circulating in loop 235 is raised in temperature by the user's body at exchange network 237 to about 30° C. Where the gas has been pre-warmed, since gas entering exchanger 227 is of a higher temperature, the overall body cooling effect is controlled (i.e., fluid temperature at network 237 is controlled). The warmed gas is then directed through valve 77 to a utilization fixture (such as a face mask for breathable air).

While fluid circulation at loops 195, 209, 223 and 235 may be accomplished by any means adequate to the task, non-electrical pumping is preferred. Pumps 240, 242, 244 and 246 are preferably, particularly where the fluid is liquid such as water or water and antifreeze, pneumatic pumps connected into gas outflow lines 248, 250, 252 and 254 from heat exchangers 183, 185, 215 and 217, and into fluid circulation loops 195, 209, 223 and 235. The pneumatic pumps utilize the pressure drop of gas moving thereacross to circulate the fluid in their respective loops.

While again not required, the pumps are preferably variable rate pumps capable of increasing fluid flow rates in the fluid circulating loops responsive to the rate of use of gas through the system and thus moving through the pumps. For example, in the case of air, increased respiratory rate of a user (indicative of work exerted by the user's body) will increase fluid flow rate through networks 211 and 237 and exchangers 185 and 217 thus increasing the rate of cooling of the body precisely at the time that the user demands increased cooling due to an increased work rate.

The pumps are preferably centrifugal or turbine pneumatic pumps capable of operation at gas pressures up to about 1250 psi and providing variable liquid flow rates between about 0.05 and 1 cubic feet per hour at pressures up to about 20 psi. Materials used in construction may be mostly aluminum and nylon, and, though designed to withstand normally cold ambient temperatures, because of placement at the outflow lines form the heat exchangers need not be designed for cryogenic temperatures.

Valves 182 and 213 are preferably automatically controlled by a processor for switching responsive to sensed body temperature and/or air temperature inputs to the processor. Garment 167 as illustrated in FIG. 15 may be either a one or two piece garment of types heretofore known. Heat exchangers 183, 185, 215 and 217, when used with a liquid secondary loop, are designed to provide heat exchange without freezing the liquid in the presence of low flow rates (of the cold gas between about 0.05 and 0.25 cubic feet per hour, and of the liquid between about 0.2 to 1.0 cubic feet per hour).

Figure 16:
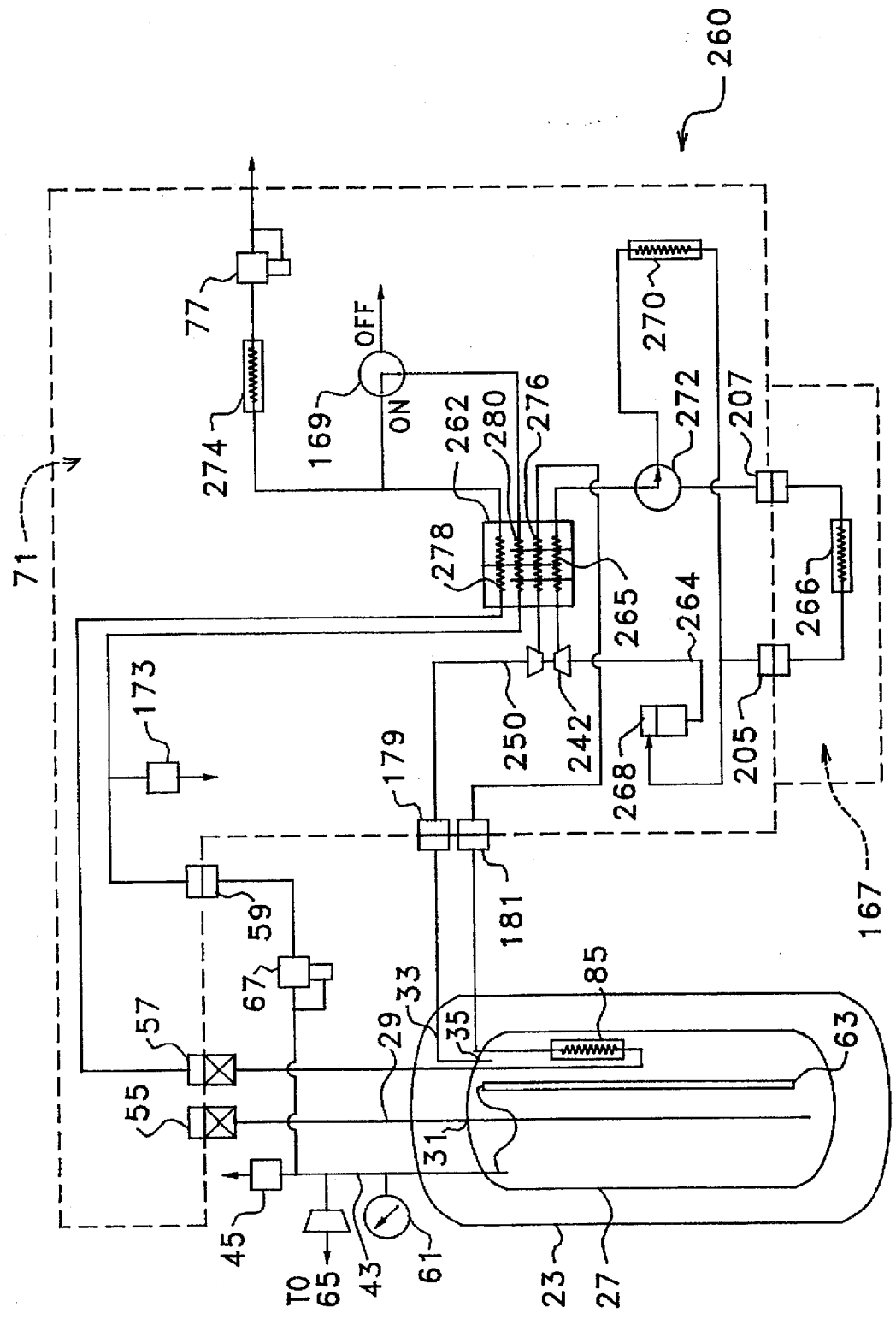
FIG. 16 is a second embodiment of the body cooling system of this invention.

A second embodiment 260 of the body cooling system of this invention is illustrated in FIG. 16. The system illustrated is the same in most regards to that heretofore shown (like elements being indicated by like numbers). However, heat exchanger 262 now combines all heat exchange functions of exchangers 171, 185 and 217 shown in FIG. 14 into a single heat exchange unit. A single fluid circulation loop 264 in circulation with fluid heat exchange conduit 265 of exchanger 262, and including a unified circulation network 266 at garment 167, is provided with fluid supply reservoir 268 at carriage unit 71. Pre-warming heat exchanger 270 (performing the control function of heat exchangers 183 and 215 as shown in FIG. 14) is also located at the carriage structure and is integral with fluid circulation loop 264. Automatic control valve 272 (processor controlled as heretofore discussed with regard to valves 182 and 213) is located in loop 264 for control of fluid flow within the loop. Additional backup heat exchanger 274 is provided to insure adequate conditioning of the mixed gas before use as may be necessary, for example, as a safety feature in a breathing system.

Exchanger 262 includes gas conduits 276, 278 and 280, conduits 276 and 278 connected in flow paths and for the functions as heretofore described for conduits 201 and 227 of exchangers 185 and 217 in FIG. 14. Gas conduit 280 is connected in a flow path and for the function as hereto described for exchanger 171 in FIG. 14.

As may be appreciated from the foregoing, an improved integrated system and method for body cooling and mixed gas conditioning are provided for use with cryogenic fluid containment and delivery apparatus.

What is claimed is:

1. A self contained, cryogenic mixed gas single phase storage and delivery system for body cooling, gas conditioning and gas utilization at a utilization fixture comprising:

a containment vessel for receiving the mixed gas at cryogenic temperature and at or above supercritical pressure so that said fluid is in a single phase when received in said containment vessel and having a first outlet connection for selective expulsion of the mixed gas contained at said containment vessel therethrough, said containment vessel having a passive heat exchanger routed therein and including an inlet connection and a second outlet connection;

a suit configured to be worn on a body to be cooled, said suit including a fluid circulation network having connection means for association of said fluid circulation network; and a body mountable pack including means for releasably maintaining said containment vessel therein and including first heat exchange means therein having a gas conduit and a fluid conduit, said gas conduit releasably connectable between said first outlet connection of said containment vessel and said inlet connection of said passive heat exchanger of said containment vessel, and said fluid conduit releasably connectable with said connection means of said fluid circulation network of said suit, said first heat exchange means for heat exchange between mixed gas received through said first outlet connection of said containment vessel and fluid at said fluid circulation network to cool fluid at said fluid circulation network of said suit for body cooling and warm mixed gas for return to said passive heat exchanger of said containment vessel to introduce sufficient heat into said containment vessel so that mixed gas remaining in said containment vessel is in a single phase, said pack further including second heat exchange means therein having a gas conduit and a fluid conduit, said gas conduit of said second heat exchange means releasably connectable between said second outlet connection of said passive heat exchanger of said containment means and the utilization fixture, and said fluid conduit of said second heat exchange means releasably connectable with said connection means of said fluid circulation network of said suit, said second heat exchange means for heat exchange between mixed gas received from the passive heat exchanger and fluid at said fluid circulation network to cool fluid in said fluid circulation network of said suit and warm mixed gas for utilization.

2. The system of claim 1 further comprising pumping means at said pack and connected with said fluid circulation network and between said first outlet connection of said containment vessel and the utilization fixture, said pumping means utilizing the mixed gas being delivered to the utilization fixture from said containment vessel for moving fluid through said fluid circulation network.

3. The system of claim 2 wherein said pumping means is a pneumatic pump.

4. The system of claim 1 wherein said fluid circulation network includes first and second fluid circulation loops, said fluid conduit of said first heat exchange means being releasably connectable at said connection means for heat exchange at said first loop and said fluid conduit of said second heat exchange means being releasably connectable at said connection means for heat exchange at said second loop.

5. The system of claim 2 wherein the mixed gas is air, and wherein said pumping means is a variable rate pump for moving fluid through said fluid circulation network at a variable rate determined by rate of use of air through the utilization fixture.

6. The system of claim 1 further comprising third, selectively actuateable, heat exchange means at said pack for selectively controlling cooling level of fluid in said fluid circulation network.

7. The system of claim 6 wherein said third, selectively actuateable, heat exchange means includes first and second selectively actuateable heat exchangers for selectively pre-warming the air received at either of said first and second heat exchange means.

8. The system of claim 1 further comprising relief means connected with said containment vessel and biased to ambient pressure for relieving excessive pressure in said containment vessel, and valve means at said pack for selectively directing mixed gas expelled at said relief means to said second heat exchange means.

9. An air storage and delivery system providing both body cooling and breathable air to a user comprising:

a pressure vessel for containing air received at cryogenic temperature and at a pressure so that the air in said vessel is in a single phase, said vessel having an outlet and an internal passive heat exchanger for introducing heat into said pressure vessel at a rate determined by rate of expulsion of air from said pressure vessel through said outlet to thereby maintain the air remaining in said vessel in a single phase;

a breathing unit connectable with said internal passive heat exchanger of said pressure vessel;

a garment having a fluid circulation network including connection means for association of said fluid circulation network; and a body mountable pack having structure for receiving and releasably maintaining said pressure vessel thereat, said pack having incorporated thereinto first heat exchange means releasably connectable with said connection means of said fluid circulation network of said garment and between said outlet from said pressure vessel and said internal passive heat exchanger of said pressure vessel for receiving air from said pressure vessel through said outlet and conducting the air for heat exchange with fluid in said fluid circulation network of said garment to both cool fluid in said fluid circulation network for body cooling and warm the air for use at said internal passive heat exchanger of said pressure vessel.

10. The system of claim 9 further comprising second heat exchange means connected between said outlet from said pressure vessel and said breathing unit for conducting the air for heat exchange with fluid in said fluid circulation network of said garment to both cool fluid in said fluid circulation network and warm the air for use at said breathing unit.

11. The system of claim 10 wherein said fluid circulation network includes first and second fluid circulation loops at different parts of said garment, said first heat exchange means being connectable for heat exchange at said first loop and said second heat exchange means being releasably connectable at said connecting means for heat exchange at said second loop.

12. The system of claim 9 further comprising a variable rate pump for moving fluid through said fluid circulation network at a variable rate determined by rate of use of air through said breathing unit.

13. The system of claim 9 wherein said pressure vessel includes a vent line having pressure regulating means connected thereat to enable loading of said cryogenic temperature air at or above supercritical pressure in said pressure vessel to capacity of said pressure vessel.

14. A method for storing and delivering mixed gas to provide both body cooling and conditioning of the mixed gas for use comprising the steps of:

loading cryogenic temperature mixed gas into a container at a pressure so that the mixed gas is in a single phase in the container;

mounting said container on a body mountable pack for carriage by a user;

selectively expelling the mixed gas from said container;

circulating fluid through a garment worn by the user at a rate determined by sensed work rate of the user, said fluid thus being warmed by body heat;

exchanging heat between said circulating fluid and said expelled mixed gas at said pack to cool said circulating fluid to thus cool the body and to warm said expelled mixed gas; and utilizing said warmed expelled mixed gas after heat exchange with said circulating fluid to introduce heat into said container to maintain mixed gas remaining in said container in a single phase.

15. The method of claim 14 further comprising the step of utilizing movement of said expelled mixed gas to circulate said fluid.

16. The method of claim 14 further comprising selectively prewarming said expelled mixed gas to selectively control cooling level of said fluid.

17. The method of claim 14 wherein the mixed gas is air, and wherein the step of exchanging heat includes exchanging heat in first and second stages, said first stage to cool said fluid and warm said expelled air for use in maintaining air remaining in said container in a single phase, and said second stage to cool said fluid and warm said expelled air for breathing.

* * * * *